United States Patent
Beyersdorf

(10) Patent No.: US 12,357,756 B2
(45) Date of Patent: *Jul. 15, 2025

(54) DEVICE FOR TREATING AN INDIVIDUAL SUFFERING FROM CARDIAC INSUFFICIENCY, CARDIAC ARREST, CIRCULATORY ARREST OR STROKE

(71) Applicant: RESUSCITEC GMBH, Freiburg (DE)

(72) Inventor: Friedhelm Beyersdorf, Freiburg (DE)

(73) Assignee: RESUSCITEC GMBH, Frieburg (DE)

( * ) Notice: Subject to any disclaimer, the term of this patent is extended or adjusted under 35 U.S.C. 154(b) by 462 days.

This patent is subject to a terminal disclaimer.

(21) Appl. No.: 17/736,231

(22) Filed: May 4, 2022

(65) Prior Publication Data
US 2022/0257861 A1  Aug. 18, 2022

Related U.S. Application Data

(60) Continuation of application No. 16/418,451, filed on May 21, 2019, now Pat. No. 11,351,303, which is a
(Continued)

(30) Foreign Application Priority Data

Oct. 12, 2009  (DE) .................... 10 2009 045 589.2

(51) Int. Cl.
*A61M 5/172* (2006.01)
*A61B 5/1455* (2006.01)
(Continued)

(52) U.S. Cl.
CPC ....... *A61M 5/1723* (2013.01); *A61B 5/14557* (2013.01); *A61M 1/34* (2013.01);
(Continued)

(58) Field of Classification Search
CPC ............ A61B 5/14539; A61B 5/14546; A61B 5/14557; A61B 5/157; A61M 1/34;
(Continued)

(56) References Cited

U.S. PATENT DOCUMENTS

| | | |
|---|---|---|
| 5,195,942 A | 3/1993 | Weil |
| 5,308,320 A | 5/1994 | Safar |

(Continued)

FOREIGN PATENT DOCUMENTS

| | | |
|---|---|---|
| DE | 102008024471 | 12/2008 |
| EP | 1021084 | 7/2000 |

(Continued)

OTHER PUBLICATIONS

Daniele, S, et al.; "Brain Vulnerability and Viability After Ischaemia", Nature Reviews Neuoscience, published online Jul. 21, 2021. www.nature.com.org, 20 pages.

*Primary Examiner* — Nicholas J. Weiss
*Assistant Examiner* — Brandon W. Levy
(74) *Attorney, Agent, or Firm* — Fitch, Even, Tabin & Flannery LLP

(57) ABSTRACT

The invention relates to a device for treating an individual suffering from cardiac or circulatory arrest or from a stroke, comprising a blood withdrawal device (BE) that is applied to the individual (P), an analysis unit (BA) which is directly or indirectly connected to the blood withdrawal device for detecting a blood analysis result (BAE) providing at least one characteristic of the blood, directly or indirectly connected to a blood return device (BR) that is applied to the individual (P) and is designed to deliver a substance to the individual via the return device (BR).

34 Claims, 4 Drawing Sheets

Related U.S. Application Data continuation of application No. 15/201,759, filed on Jul. 5, 2016, now Pat. No. 10,314,973, which is a division of application No. 13/501,248, filed as application No. PCT/EP2010/006199 on Oct. 11, 2010, now Pat. No. 9,402,952.

(51) Int. Cl.

| | | |
|---|---|---|
| *A61M 1/34* | (2006.01) | |
| *A61M 1/36* | (2006.01) | |
| *A61M 5/14* | (2006.01) | |
| *A61M 5/142* | (2006.01) | |
| *A61M 5/168* | (2006.01) | |
| *A61M 5/44* | (2006.01) | |
| *A61B 5/145* | (2006.01) | |
| *A61M 5/00* | (2006.01) | |

(52) U.S. Cl.
CPC ........ *A61M 1/3666* (2013.01); *A61M 1/3687* (2013.01); *A61M 1/369* (2013.01); *A61M 5/1408* (2013.01); *A61M 5/142* (2013.01); *A61M 5/16827* (2013.01); *A61M 5/44* (2013.01); *A61B 5/14539* (2013.01); *A61B 5/14546* (2013.01); *A61M 1/3639* (2013.01); *A61M 2005/006* (2013.01); *A61M 2005/14272* (2013.01); *A61M 2202/0208* (2013.01); *A61M 2202/04* (2013.01); *A61M 2202/0468* (2013.01); *A61M 2202/0486* (2013.01); *A61M 2202/06* (2013.01); *A61M 2202/07* (2013.01); *A61M 2205/3368* (2013.01); *A61M 2205/52* (2013.01); *A61M 2205/75* (2013.01); *A61M 2210/125* (2013.01); *A61M 2230/005* (2013.01); *A61M 2230/20* (2013.01); *A61M 2230/201* (2013.01); *A61M 2230/202* (2013.01); *A61M 2230/205* (2013.01); *A61M 2230/208* (2013.01); *A61M 2230/30* (2013.01); *A61M 2230/50* (2013.01); *A61M 2250/00* (2013.01)

(58) Field of Classification Search
CPC .... A61M 1/36; A61M 1/3639; A61M 1/3666; A61M 1/3687; A61M 1/369; A61M 5/1408; A61M 5/142; A61M 5/16827; A61M 5/1723; A61M 5/44; A61M 37/00; A61M 2005/006; A61M 2005/14272; A61M 2202/0208; A61M 2202/04; A61M 2202/0468; A61M 2202/0486; A61M 2202/06; A61M 2202/07; A61M 2202/3368; A61M 2202/52; A61M 2202/75; A61M 2210/125; A61M 2230/005; A61M 2230/20; A61M 2250/00; A61M 2230/201; A61M 2230/202; A61M 2230/205; A61M 2230/208; A61M 2230/30; A61M 2230/50; A61M 2205/3368; A61M 2205/75; A61M 2205/52; A61P 7/08
See application file for complete search history.

(56) References Cited

U.S. PATENT DOCUMENTS

| | | | |
|---|---|---|---|
| 5,494,822 A * | 2/1996 | Sadri | A01N 1/143 417/42 |
| 5,716,318 A | 2/1998 | Manning | |
| 5,843,024 A | 12/1998 | Brasile | |
| 5,879,316 A * | 3/1999 | Safar | A61M 60/546 604/6.11 |
| 5,938,636 A | 8/1999 | Kramer | |
| 7,387,798 B2 | 6/2008 | Wang | |
| 9,402,952 B2 * | 8/2016 | Beyersdorf | A61M 5/16827 |
| 10,086,139 B2 * | 10/2018 | Beyersdorf | A61M 1/3666 |
| 10,314,973 B2 * | 6/2019 | Beyersdorf | A61M 1/369 |
| 11,351,303 B2 * | 6/2022 | Beyersdorf | A61M 5/16827 |
| 2005/0101907 A1 | 5/2005 | Sondeen | |
| 2008/0294252 A1 | 11/2008 | Myklebust | |

FOREIGN PATENT DOCUMENTS

| | | |
|---|---|---|
| WO | 9421195 | 9/1994 |
| WO | 9632157 | 10/1996 |
| WO | 2005025646 | 3/2005 |
| WO | 2006091650 | 8/2006 |

\* cited by examiner

DEVICE FOR TREATING AN INDIVIDUAL SUFFERING FROM CARDIAC INSUFFICIENCY, CARDIAC ARREST, CIRCULATORY ARREST OR STROKE

CROSS REFERENCE TO RELATED APPLICATIONS

This application is a continuation of application Ser. No. 16/418,451, which is a continuation of application Ser. No. 15/201,759 now U.S. Pat. No. 10,314,973, which is a divisional of application Ser. No. 13/501,248 now U.S. Pat. No. 9,402,952, which applications are incorporated herein by reference in their entirely. Reference is also made to DE 10 2009 045 589.2 filed Oct. 12, 2009 and to PCT/EP2010/006199 filed Oct. 11, 2010 of which applications are incorporated herein by reference in their entirety.

BACKGROUND OF THE INVENTION

Field of the Invention

The invention relates to a device for treating an individual suffering from cardiac insufficiency, cardiac arrest, circulatory arrest or stroke.

Description of the Prior Art

Given the current level of knowledge and the current therapeutic methods, individuals, more particularly patients, who have suffered cardiac arrest, can only be resuscitated without damage to the brain or the heart functions if cardiopulmonary resuscitation is successfully carried out within a period of three to five minutes after the cardiac arrest has occurred. Resuscitation carried out with a further time delay inevitably leads to severe cerebral damage due to reperfusion with normal blood which causes massive damage to the ischaemic tissue.

Ischaemic and reperfusion modifications in tissues mainly play a central role in heart surgery. For example, myocardial ischaemia is either induced by the surgeon himself, for instance as part of global ischaemia through aortic clamping, or also during a heart transplant and/or regionally in "off-pump surgery" for application of a coronary by-pass. However, emergency operations are also performed on patients with myocardial ischaemia who, for example, are suffering from cardiogenic shock, acute coronary occlusion or a condition immediately after resuscitation. For these reasons heart surgeons have been intensively occupied with ischaemia and reperfusion phenomena for decades.

In accordance with current knowledge, it can be assumed that ischaemia, even long-lasting ischaemia, only causes relatively small structural damage to the heart muscle. However, if after such an ischaemic attack the myocardium is reperfused with normal blood under "physiological" conditions, an additional damaging mechanism occurs explosively, which in the meantime has been well researched as "reperfusion damage". On reperfusion of an ischaemically damaged myocardium with normal blood, processes suddenly occur which can definitively destroy the already damaged tissue.

To prevent or completely hinder the reperfusion damage occurring through reperfusion with normal blood, concepts have been developed, which after revascularization, initially endeavour to treat the ischaemically damaged myocardium, whereby both the composition of the initial reperfusate and the conditions of the initial perfusion are aimed at treating the damage occurring during the ischaemia and/or ruling out possibly occurring reperfusion damage right from the start.

The concept of controlled reperfusion is based on the one hand on modifying the initial reperfusate differently from the body's own blood as well as modifying the conditions of the initial reperfusion.

In connection with this, DE 696 31 046 T2 discloses a device for treating a patient with cardiac arrest which uses the known method of selective aortic arch perfusion, SAAP in short, in which in order to carry out relatively isolated perfusion of the heart and brain, a balloon occlusion catheter is applied, usually via the patient's femoral artery, to the location of the descending aortic arch and then dilated, after which an oxygenated blood substitute solution, for example perfluorocarbon emulsion or a polymerized haemoglobin solution is then infused via the lumen of the SAAP catheter. The blood substitute solution, also known as a protective solution, is administered intracorporeally using a pulsing device with a pulsating rhythm. In a variant embodiment the known device has a blood withdrawal means, with which blood can be withdrawn from the patient which is taken to blood oxygenation means for oxygenation and, together with a protective solution added to the oxygenated blood, is infused into the patient via blood return means. It should be noted here that to carry out selective aortic arch perfusion and thus to use the above device, a surgical procedure and the associated clinical infrastructure are necessary.

U.S. Pat. No. 5,195,942 discloses a comparable procedure for resuscitating a person, in which by inflating a balloon catheter in the region of the ascending aorta in order to increase the blood flow into the coronary arteries, a blood-compatible, oxygen liquid is injected for flowing on into the coronary arteries.

U.S. Pat. No. 7,387,798 B2 describes a method for the resuscitation of patients suffering from cardiac arrest, in which a liquor fluid is taken from the subarachnoid area of the patient's central nervous system. An artificially composed cerebrospinal fluid containing a large number of components, such as sodium, potassium, calcium, magnesium, water, polypeptides, insulin and ATP, is then infused, whereupon conventional cardiopulmonary resuscitation is carried out.

For resuscitating a patient or an animal, U.S. Pat. No. 5,416,078 discloses administering a solution of Deferoxamine with water-soluble biopolymers to the patient to be treated.

WO 94/21195 describes administering an A3 adenosine receptor agonist for preparing the organ in order to protect it against ischaemic damage.

In EP 1 021 084 B1 a method of eliminating or reducing ischaemic damage to an organ is set out. Here, the damaged organ is rinsed with a buffered physiological solution in order to remove acidic products which have accumulated in the organ during the period of oxygen deficiency.

U.S. Published Application 2005/0101907 A1 describes an automatic system for the resuscitation of a patient in which a single fluid is infused in relation to the fluid inflow as function of physiological parameters of the patient.

A comparable automatic infusion system for treating trauma patients is disclosed in U.S. Pat. No. 5,938,636, for infusion of an administered fluid into the patient with the infusion pressure and infusion flow being sensor-recorded and computer-monitored.

DE 10 2008 024 471 A1 describes a heart-lung by-pass device which can be connected to a patient by one tube to the arterial and one tube to the venous blood vessel system. Extracorporeally, between the tubes, there is a blood flow line along which bi-directionally operating pumps and a fluid reservoir can be provided. Controllable fluid control valves fitted with sensors are also arranged along the blood flow line. Through bi-directional pump operation, the lungs assume the function of the oxygenators of the heart-lung by-pass device.

U.S. Pat. No. 5,308,320 describes a portable resuscitation device for cardiac arrest patients having blood withdrawal means, a pump for moving the blood within the devices, means for oxygenating the blood and means for returning the oxygen-enriched blood back into the blood circulation.

SUMMARY OF THE INVENTION

The invention is a device for providing full resuscitation of a patient without the risk of ischaemic damage during a period of time between the onset of the cardiac arrest and the initiation of resuscitation measures which is considerably greater than the previous critical time window of 3 to 5 minutes. The device allows as fully automatic resuscitation as possible so that no complicated therapeutic precautions have to be taken in situ. The device also is lightweight and portable and independently operable as possible so that it can be used as an instrument for emergency medicine on site. The device is useful for a cardiac arrest, and for cardiac insufficiency or a stroke, based on the same principles.

The invention exerts, by way of at least one sensor-supported blood analysis of the individual's blood, an individual blood analysis-dependent influence on the blood taken from the individual so that an individually selected substance or an individually produced substance mixture is added or mixed to the blood taken from the individual to obtain "modified blood." The thus obtained "modified blood" is reperfused into the individual as a reperfusate with the goal of partially or fully preventing the ischaemic tissue damage otherwise occurring on activation of the natural or artificially-supported blood circulation system or on initial blood supply to areas of tissue disconnected from the natural blood circulation for a shorter or longer period.

The device in accordance with the invention for treating an individual with cardiac arrest or stroke, includes a blood withdrawal device attachable to the individual for withdrawing at least part of the blood from an individual, an analysis unit directly or indirectly connected to the blood withdrawal means for recording and providing at least one property of the blood in the form of blood analysis result, an operative unit, which is indirectly or directly connected to a blood return device attachable to the individual and designed to administer a substance to the individual via the return means. The operative unit has at least one reservoir in which at least two substances are stored. The reservoir unit is combined with a dosage unit, which, taking into consideration a blood analysis result determined by the analysis unit, selects at least one of the two substances or prepares a mixtures of at least two of the substance. The at least one selected substance or the mixture can then be applied to the individual directly or indirectly via the blood return device.

The individual is, more particularly, a human or animal patient. The terms "patient" and "individual" are used synonymously here. Cardiac insufficiency is understood, for example, as a traumatic or pathological reduction in the output of the heart, which may be caused by a heart attack, cardiogenic shock or heart failure.

In one variant, the device of the invention also has a sensor device, recording at least one property of the individual's blood, which generates a sensor signal, which is then evaluated by the analysis unit and made available as a blood analysis. The analysis unit is fundamentally suitable for working with the sensor unit so that a sensor signal determined/generated by the sensor unit can be transmitted from the sensor unit to the analysis unit. The device can be produced with already known sensors.

The sensor unit can comprise a plurality of sensors, of which each sensor records at least one parameter or property of the blood.

In one variant, the sensor unit is designed as a non-invasive component which can be directly or indirectly attached to the individual.

The blood withdrawal device for taking the blood are envisaged and set up to withdraw at least part of the blood from an individual before the blood is influenced by the operative unit. For this the blood withdrawal device is, for example, invasively attachable to the individual. In this way at least two liters, more particularly at least three liters, more particularly at least four liters, or more particularly all the blood in the individual's blood vessels, can be withdrawn.

Through the blood return device, the withdrawn and treated or influenced blood, that is the "modified blood," can be returned into the body of the individual. The return means can also be invasively attached to the individual.

On the one hand, at least one substance in the form of an additive to the blood in the patient, for example, can be administered by way of an injection into the infusion, or the patient's blood is removed from the patient by way of blood withdrawal device and extracorporeally enriched or treated with the at least one substance which is then reperfused into the patient in the form of "modified blood." It is also conceivable to remove essentially all the blood from a patient and, instead of this blood, to return the "modified blood" or a solution, individually adapted to the patient and containing at least one substance, directly to the patient in order to then be able to initiate the process of resuscitation without tissue damage.

In one embodiment, the sensor unit is directly or directly connected to the blood withdrawal device.

For the purpose of modification and/or manipulation of the patient's own blood individually adapted to the patient situation, in one variant the operative unit is controlled or regulated by an evaluation and control unit on the basis of the analysis result which represents the patient's current condition.

Advantageously, the analysis unit, the operative unit, the evaluation and the control unit are a portable and standard unit, in which the sensor unit is preferably part of the standard unit.

The sensor unit generates the sensor signal which represents the at least one property of the blood taken from the patient and can be transmitted by cable or wirelessly to the analysis unit, whereby on the basis of the analysis results, the evaluation and control unit generates control or regulating signals. These can be used, for example, to select or dose the type and/or quantity the substance or substance mixture to be added. Here, the sensor unit records at least one of the following parameters: pH value, partial oxygen pressure ($pO_2$), partial carbon dioxide pressure ($pCO_2$), potassium content (K), sodium content (Na), calcium content (Ca), base excess (BE), lactate value (La) and glucose content (Gu).

The device in accordance with the invention is preferably also portable and easy to operate, more particularly as a fully autonomous unit, so that it is not necessarily exclusively usable by medical specialist personnel. One form of embodiment comprises a portable handy unit, from which only two tubes extend, which on the patient side are connected to the blood vessel system. One tube is for taking the blood from the patient, via which the patient's blood automatically flows out into the unit, in which an analysis of the blood and corresponding modification of the blood take place. The appropriately "modified blood" is then reperfused into the patient via the other tube. Alternatively, this device also makes it possible, before the "modified blood" is returned to the patient, to administer to the patient an individually composed perfusion solution, the composition of which depends on the result of the analysis of the patient's own blood. For a successful treatment outcome, it is therefore conceivable in a first step to largely substitute the blood with an individually composed perfusion solution. Only later on during the treatment is the aforementioned "modified blood" administered, possibly after successfully carrying out further resuscitation measures.

In one variant, the operative unit dispenses the at least one substance to the individual or the blood in dosed form at the correct temperature and/or pressure.

Preferably, a monitoring unit is provided which has at least one measuring device for recording the at least one parameter of the individual, which is selected from the group of physiological parameters of the individual, comprising mean arterial pressure, central nervous pressure, pulmonary arterial pressure, oxygen saturation and blood temperature, whereby the monitoring unit is connected to an evaluation and monitoring device for at least unilateral data exchange.

Fundamentally, the blood is taken from the patient as a bodily fluid. However, the embodiments of the device relating to blood as the bodily fluid can also be used for other bodily fluids in an analogous manner.

The blood withdrawal device to be applied to the patient is preferably connected via a blood flow path, in the simplest case in the form of a hollow tube, to the blood return device applicable to the patient, whereby, more particularly, along the blood flow path the reservoir unit of the operative unit is provided, which contains at least two substances, and from which at least one of the substances to be selected or a substance mixture can be added to the blood flow path or the blood return device.

Along the blood flow path a heat exchanger unit can also be provided which is directly or indirectly connected to the return means. At least one conveying device integrated along the blood flow path is also for adjusting the blood flow along the blood flow path in order to assure simple transporting of the blood from the individual's body and of the modified blood into the individual's body. Preferably, for returning the blood to the body a further, separate conveying device is provided, with which flow characteristics can be set which are individual and above all independent in terms of pulsability, flow pressure and speed.

For controlling all present conveying devices as well as the heat exchanger unit, the evaluation and control unit generates further signals, so that ultimately the flow pressure, the flow rate and/or temperature of the at least one substance or the "modified blood" to be returned to the patient can be set in a predetermined manner.

The analysis unit with its sensor unit is also arranged along the blood flow path, so that in terms of individual blood parameters, more particularly a large number of blood parameters, the blood can be analyzed and a blood analysis result is made available for further evaluation. The analysis preferably takes place online, that is on site, while the blood is being taken from the patient by the blood withdrawal device.

Taking into consideration the blood analysis result determined by the analysis unit, the dosage unit connected to the reservoir unit brings a predeterminable quantity of the at least one substance from the reservoir unit and adds it into the blood flow path or to the blood return device. As a result, with the aid of the dosage unit, an individually composed reperfusate based on the current condition of the patient to be treated is produced, which is then reperfused into the patient via the applied blood return unit.

Particularly in the reperfusion of "modified blood" into the patient, but also in the simple administration of a perfusion fluid, the addition of at least one, more particularly many substances to the patient's own blood or the perfusion solution as well as the perfusion itself, takes place, with regard to the selection of the reperfusion pressure, the flow rate, the reperfusion duration and the temperature of the reperfusate, taking in consideration and adapted to the patient's current sensor-recorded blood picture. The aforementioned monitor unit can be used for this for example. In this way the selection and setting of the physiological reperfusion conditions can also take place taking into consideration the physiological parameters determined by the monitoring unit.

The aforementioned evaluation and control unit, which can, for example, be connected both to the analysis unit and to the dosage unit for the purpose of at least unilateral data exchange, is used to evaluate blood analysis results determined by the analysis unit and to determine the type and quantity of the substances to be added to the patient's own blood or the perfusion solution. The blood analysis result is evaluated in the evaluation and control unit under predetermined evaluation criteria, which can also take the physiological patient parameters recorded by the monitoring unit into consideration.

Data transmission connections in the form of conventional data transmission cables or wireless technologies are used for the at least unilateral exchange of data.

As a result of the evaluation of the blood analysis result, the evaluation and control unit generates control signals which are transmitted to the dosage unit for selecting the type and quantity of the substances to be added to the blood flow. In connection with this, the term "dosage unit" is understood as a technical device with which it is possible, from a number of substances stored in separate reservoir chambers, on the basis of defined mixing plan in which the selection of the relevant substances and the quantity of the substance to be added is defined, to make a mixture which is ultimately to be added to the patient's own blood. It is not necessary to premix the selected substances before adding them to the patient's own blood as the separate, dosable addition of individually selected substances to the blood flow path is also conceivable.

Preferably. the dosage unit has at least one mixing container, which has individually controllable dosing unit which are connected to the individual reservoir chambers. In the mixing container, a substance mixture to be added to the bodily fluid of the individual is produced in the mixing container in the form of a solution, a suspension or an emulsion. Thus, the substances stored in the reservoir chambers are not necessarily fluid and an individual substance can also be present in solid or powder form or also in the gaseous phase. For example, the following substances or substance classes from which an individual selection can be made to produce a substance mixture to be added to the bodily fluid of the individual can be stored in the individual reservoir chambers: alkaline or acidic buffer solution, substances affecting the sodium, potassium and/or calcium content, blood-thinning substances, free radical trapping agents, glutamate, aspartame, heart-rhythm-stabilizing substances (Lidocaine), substances influencing the leukocyte count, osmotically-active substances, namely salts, glucoses, proteins.

In one variant, a filter unit for blood filtering is provided along a blood flow path between the blood withdrawal device and the blood return device. This filter may include a leukocyte filter for example.

In one variant along the blood flow path between the blood withdrawal device and the blood return device, directly upstream of the blood return device a by-pass line is provided, through which some of the "modified blood" to be returned to the individual can be supplied to the analysis unit and in the event of an anomalous nominal/actual comparison, the dosage unit changes the quantity of the at least one substance supplied into the blood path flow for at least one determinable blood parameter.

In one variant, the individual components of the device are so compact and light in weight that the device is portable.

In one variant, along a blood flow path between the blood withdrawal device and the return device, an oxygenation and oxygen-depletion unit for the blood is provided in order to match the oxygen content of the modified blood to be returned to the relevant requirements.

One form of embodiment of the device in accordance with the invention includes a portable base module, hereinafter referred to as CIRD (as acronym for Controlled Integrated Resuscitation Device. The CIRD base module has an extracorporeal blood flow path which can be applied by way of suitable blood device and (blood) return device to the patient's blood circulation, more particularly in the area of the femoral artery and femoral vein. Along the extracorporeal blood flow path, the CIRD base module has a conveying device for maintaining the blood flow, an oxygenator for enriching the blood with oxygen, as well as a device for $CO_2$ depletion and finally, a leukocyte filter, and can be modularly expanded with the aforementioned blood analysis unit as well as the previously described reservoir and dosing unit.

With the aid of such a device, for the automatic operation and control of which the also previously mentioned evaluation and control unit is provided, mostly in the form of a computer unit, it is possible to quickly and automatically analyze the blood taken from a patient suffering from cardiac arrest and to determine exactly which composition of additional substances has to be added to the patient's own blood. From the result of the blood analysis, and, possibly, also taking into account the sensor-recorded physiological parameters of the patient, a reperfusate is finally automatically produced which is individually adapted to the patient and introduced into the patient under optimized conditions in terms of pulsability, flow pressure, flow rate and/or temperature. This creates ideal conditions for the initial perfusion in terms of the reperfusion pressure, the reperfusion flow and the reperfusion duration.

As the device in accordance with the invention allows continuous monitoring of the patient's own blood, the reperfusion conditions and the composition of the reperfusate can be adapted in situ or online, that is continuously, to the current condition of the patient being reperfused. More particularly, through the in situ/online measurement of certain blood parameters, such as the concentration of potassium ions, lactate, glucose or the pH value etc. as well as through the combined measurement of haemodynamic parameters by way of suitable monitoring sensors which record the flow resistance, temperature, the flow rate as well as the flow pressure etc. within the blood flow path, automatic adjustments can be made as part of the controlled whole-body reperfusion.

The device in accordance with the invention for extracorporeal whole-body reperfusion was successfully tested in experiments on pigs. Fifteen minutes after controlled induced cardiac arrest in normothermic conditions, animals could be successfully resuscitated without noticeable or measurable organ damage or neurological damage. These experiments show, for the first time. that it is possible to achieve fully functional neurological recovery, even 15 minutes after the onset of cardiac arrest, a fact which is in sharp contrast to the model and limitations of current conventional treatments. More particularly, through the lightweight and portable design of the device in accordance with the invention, completely new perspectives are opened up for emergency medicine which could result in very many patients, who today have no chance of resuscitation and/or full recovery, not only being able to be saved in future, but also to recover without neurological damage.

The subject matter of the invention is also a method of treating an individual suffering from cardiac arrest or stroke in which blood is taken from the individual which then undergoes a blood analysis, whereby taking into consideration a blood analysis result determined by the analysis unit and at least one evaluation criterion, from at least two stored substances the type and quantity of at least one of the substances or a substance mixture are determined, which in dosed form is added to the removed blood to obtain "modified blood" which is reperfused into the individual or which is reperfused into the individual in the form of perfusion solution in place of the removed blood.

In one variant of the method of the invention, the blood is taken from the individual before recording the properties and returned after adding the at least one selected substance to the blood.

In one variant, the recording, evaluation and influencing take place in a closed control cycle.

In one variant of the method of the invention, the analysis result is compared with a nominal value, and in the event of a quantitatively predeterminable deviation from the nominal value, a substance influencing the blood property forming the basis of the analysis result is selected and introduced into the individual or the blood in a quantity depending on the quantitative deviation.

In one variant of the method of the invention, at least two liters, more particularly at least three liters, more particularly at least four liters, and more particularly all the blood in the individual's blood vessels, is to be withdrawn before reperfusion of the modified blood takes place.

In one variant of the method of the invention, the blood is taken from the patient over a period of 10 seconds to 3 minutes, more particularly 20 seconds to 2 minutes, more particularly 30 seconds to 1 minute.

In one variant of the method of the invention, some of the "modified blood" is branched off for the purpose of repeated blood analysis, and if the at least one determined blood parameter deviates from the nominal value, a correction to the type and/or quantity of the at least one added substance takes place.

In one variant of the method of the invention, the procedures of taking the blood, blood analysis, adding the at least one substance to the blood or perfusion solution as well as the reperfusion of the modified blood or perfusion solution take place in situ.

In one variant of the method, in addition to the blood analysis, at least one physiological parameter of the individual is determined. Taking into consideration both the blood analysis result and also the at least one physiological parameter of the individual, the type and quantity of the at least one substance to be added to the removed blood or perfusion solution, as well as the pressure, flow rate and temperature of a modified blood flow or solution to be reperfused into the individual, are selected.

In one variant of the method of the invention, the reperfusion of the "modified blood" or perfusion solution into the individual takes place at least two different parts of the body each with different reperfusion parameters in terms of pressure, flow rate, temperature and/or reperfusion duration.

In one variant of the method of the invention, the blood is taken at a controlled flow rate of at least 1 l/min, more particularly from 6 to 8 l/min.

All the above-mentioned method variants can be combined with each other in any way and order.

BRIEF DESCRIPTION OF THE INVENTION

The invention is described below, without restricting the general concept of the invention, by way of examples of embodiments with reference to the drawings, in which.

Figure 4:
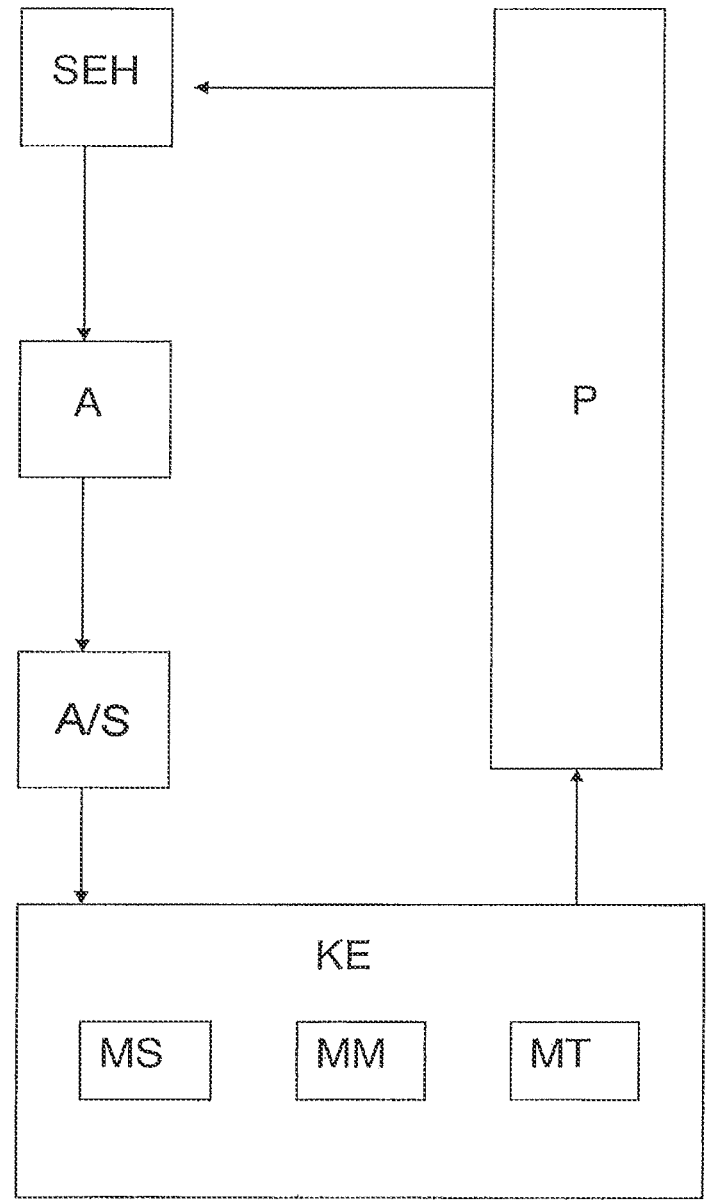

FIG. 4 a generalized block diagram of an example of embodiment.

DESCRIPTION OF EMBODIMENTS OF THE INVENTION

Figure 1:
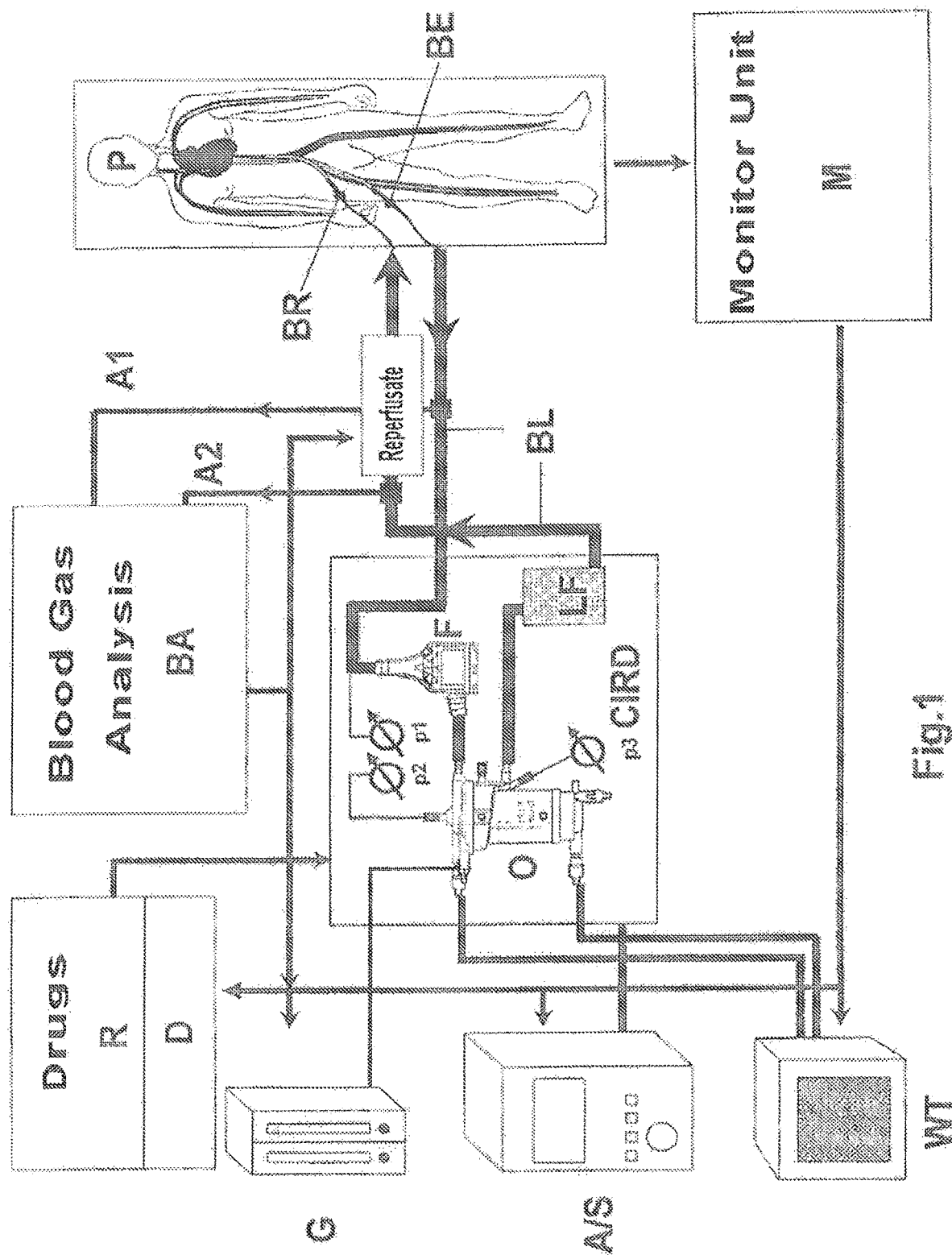
FIG. 1 shows a block diagram of an illustration of the individual components of an example of embodiment.

In FIG. 1, a block diagram illustrating all the components of an embodiment of a device in accordance with the invention is shown. The use of the device is explained in more detail using the example of a human patient P as an individual who has suffered a cardiac arrest. Applied to the patient P in the area of femoral vein in order take blood are a blood withdrawal device BE shown as a catheter, from which a blood flow path BL extends extracorporeally, which passes through various technical components and from which at various points lines branch off and into which at various points lines open, which are discussed in more detail below. Finally the blood flow path BL enters the patient again, more particularly in the area of the femoral artery to which a blood returns device BR shown as a catheter is also applied.

For controlled blood withdrawal from the patient P and for setting the reperfusion parameters under which the device to be described returns "modified blood" or reperfusate into the patient's blood circulation, a conveying unit F is provided along the blood flow path BL, which is more particularly in the form of a centrifugal pump and is to be seen as a component of the lightweight and portable CIRD. The conveying unit F can also be variably adjusted in terms of conveying output, conveying characteristics and duration that is pressure, duration and pulsability, via an evaluation and control unit A/S yet to be described in more detail. In addition, the portable CIRD has an oxygenator O, with which the blood taken from the patient is enriched with oxygen. In certain cases, with the aid of the oxygenator, it is also possible to deplete oxygen from the patient's own blood. There is also a gas blender G, which influences the blood $CO_2$ content, usually in the form of depletion of the $CO_2$ content in the patient's own blood. For individual temperature control of the blood flow within the blood flow path BL, the oxygenator O is also connected to a heat exchanger unit. The heat exchanging characteristics are influenced in a controlled manner by the evaluation and control unit A/S. Finally, the portable CIRD unit comprises a leukocyte filter through which the leukocyte content of the patient's blood can be influenced.

A first by-pass line A1 is provided in the blood flow path BL directly leaving the patient, via which some of the patient's blood is branched off into an analysis unit BA in which the patient's blood is analyzed by sensors with respect to various blood parameters.

In an expanded form of embodiment, the device of FIG. 1 may be supplemented with further functional units, which are able to modify or manipulate the patient's blood in the following manner.

Units are thus provided for influencing the patient's blood through extracorporeal pressure exertion on the patient in such a way that in terms of time and space the pressure exertion takes place in a predeterminable manner on the patient evenly or selectively. Such units for the mechanical influencing of the patient's blood can alternatively also be applied invasively and for intracorporeal pressure exertion on the patient's blood.

In addition, units for the thermal influencing of the patient's blood for extracorporeal temperature control can be provided and designed so that in terms of time and space, the temperature control takes place in a predeterminable manner on the patient evenly or selectively. Such units for the thermal influencing of the patient's blood can alternatively also be applied invasively and for intracorporeal temperature control of the patient's blood so that in terms of space and time the temperature control takes place in a predeterminable manner within the patient evenly or selectively.

Preferably, to return the blood to the body of the patient P, along the blood flow path, before or after the leukocyte filter LF at least one further, separate conveying device (not shown) can be provided, with which conveying characteristics can be set which are individual and above all independent in relation to pulsability, flow pressure and speed.

Figure 2:
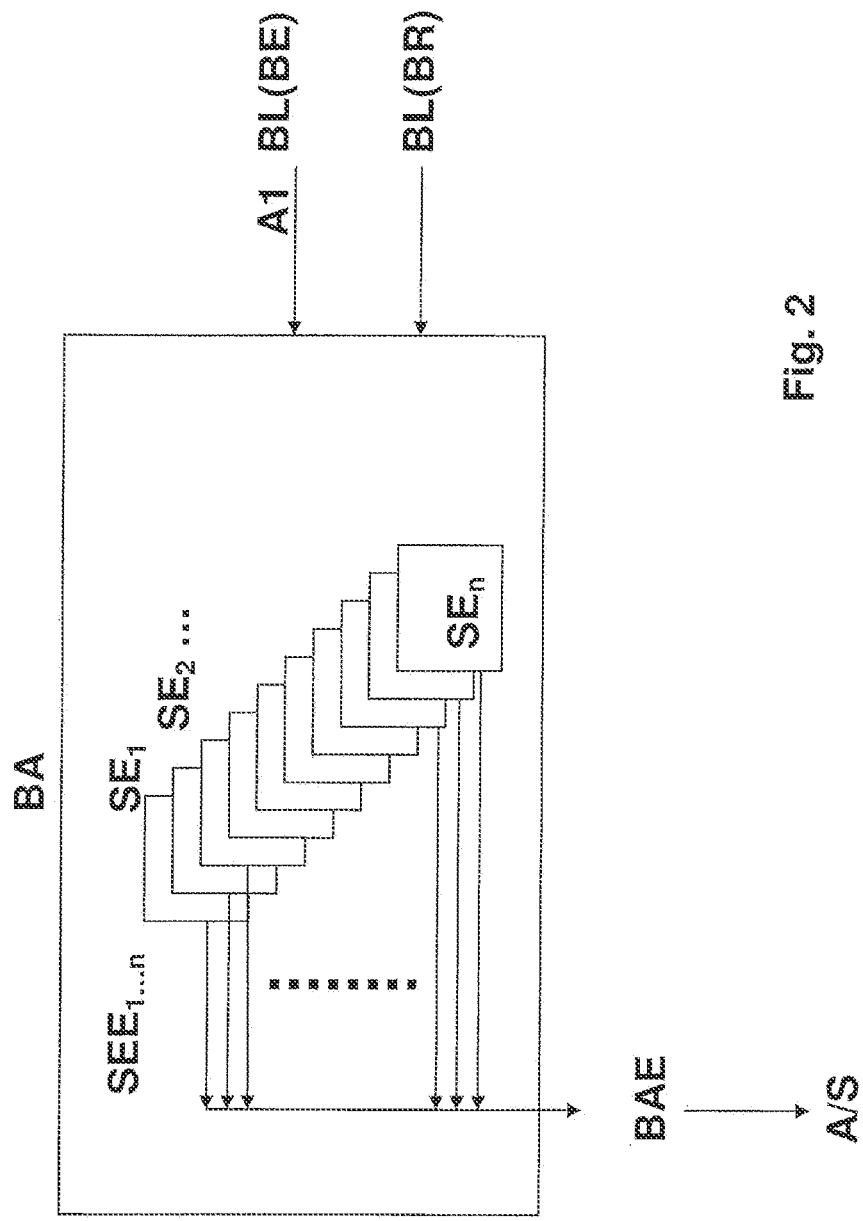
FIG. 2 shows a schematic view of the analysis unit.

In FIG. 2, an analysis unit BA is shown schematically for more detailed explanation. It is assumed that via line A1, part of the patient's blood reaches the blood analyzing analysis unit BA. Within the analysis unit BA, more particularly in the form of a sensor unit, a number of individual sensors $SE_1$ to $SE_n$ are provided, which analyze the blood with regard to various blood parameters. Advantageously brought together in the analysis/sensor unit are known sensors each one of which is able to record at least one of the following non-exhaustively listed parameters: pH-value, partial oxygen pressure ($pO_2$), partial carbon dioxide pressure ($pCO_2$), potassium content (K), sodium content (NA), calcium content (Ca), the base deviation designated as BE, also known as base excess/base deficit with which metabolic disorders of the acid-base balance can be detected, lactate value (La), glucose content (Gu) to name but a few.

Each individual sensor $SE_{1 \ldots n}$ determines one blood parameter $SEE_{1 \ldots n}$, characteristic of the patient's blood, which together produce the so-called blood analysis result BAE which reflects the current quality of the patient's own blood. More particularly, the blood analysis result is transmitted via a data transmission cable to the evaluation and control unit A/S in which the blood analysis result BAE undergoes separate analysis and evaluation based on medical evaluation criteria.

The purpose of the device in accordance with the invention is ultimately to transform, through the addition of certain substances, the patient's blood into a modified state which can be characterized in the fact that the specially "modified blood" or the reperfusate should not cause any tissue damage during initial reperfusion into the patient for the purpose of the patient's resuscitation. In addition, it is intended to reduce/heal ischaemic damage which may have already occurred in certain tissue areas.

Figure 3:
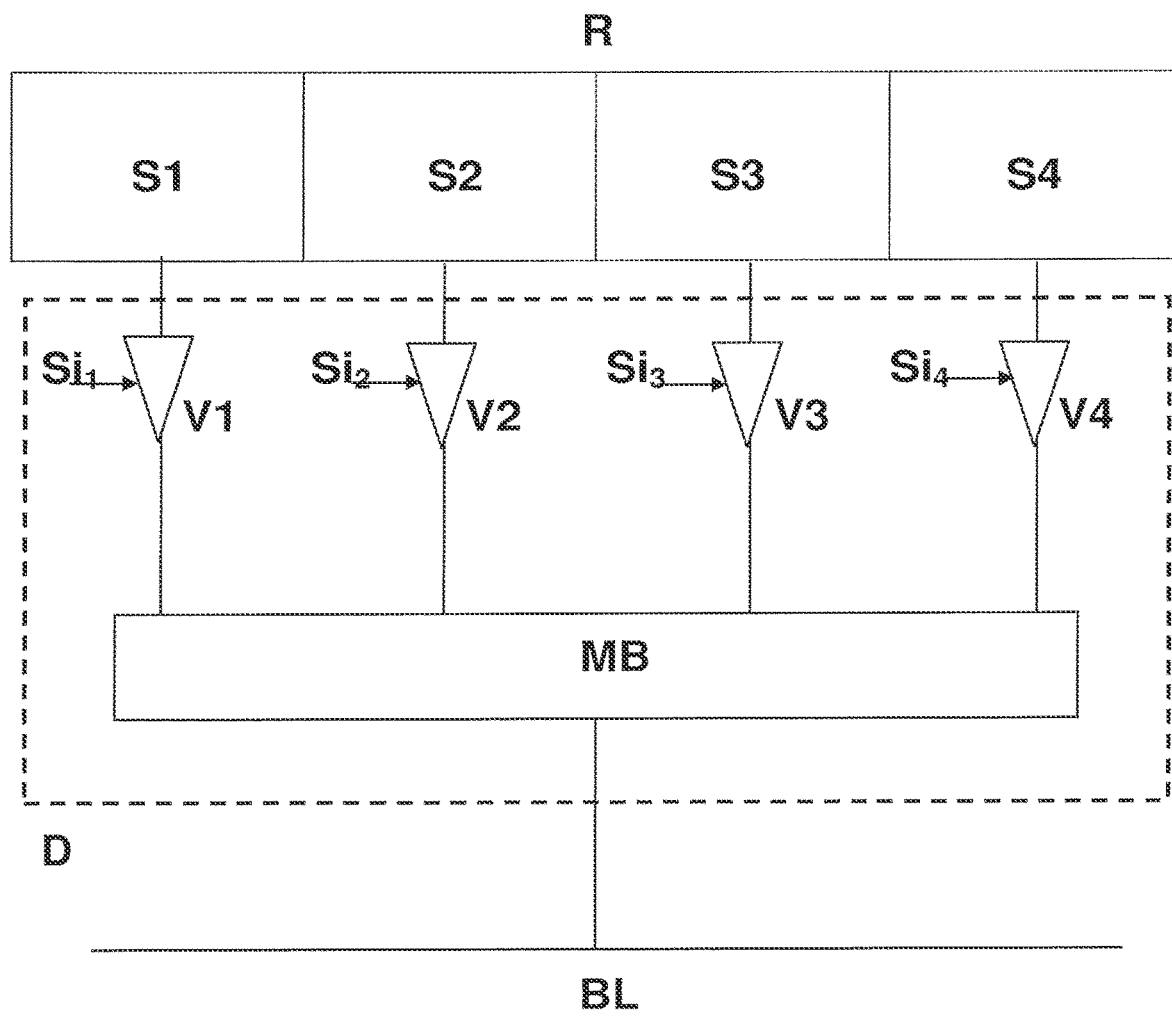
FIG. 3 shows a schematic view of a reservoir and dosage unit.

Within the evaluation and control unit A/S the current sensor-recorded individual blood parameters $SEE_{1...n}$ of the patient's blood are compared with blood parameter-specific references or nominal values, which are to be restored through modification of the patient's blood. In accordance with such an evaluation the type and quantity of the relevant substances to be added to the patient's blood are determined. The evaluation/control unit is in informal communication with a reservoir unit R as well as a dosage unit D combined therewith, which are both shown schematically in FIG. 3. In accordance with FIG. 3 the reservoir unit R comprises four individual reservoir chambers in which four different substances $S_1$, $S_2$, $S_3$ and $S_4$ are stored. More such reservoir chambers can of course be provided, that is in general reservoir chambers for storing n different substances. The individual reservoirs are each connected to a mixing container MB, whereby along the connection lines dosage units in the form of stop valves $V_1$, $V_2$, $V_3$ and $V_4$ are provided. Depending on the current blood analysis result BAE and the additive requirement determined by the evaluation/control unit for the substance to be mixed to the patient's blood, the evaluation/control unit generates control signals $Si_1$, $Si_2$, $Si_3$, $Si_4$ for operating the dosage units $V_1$ to $V_4$. Finally, the mixture of the individual substance prepared in the mixing container MB is introduced into the blood flow path BL.

In a variant, a monitoring unit M (see FIG. 1) is provided, which via sensors applied to the patient P, records physiological patient parameters, for example the mean arterial pressure, the central venous pressure, the pulmonary arterial pressure, oxygen saturation, as well as body temperature, to name but a few. The physiological patent parameters are also transmitted by the monitoring unit M to the evaluation and control unit A/S, where after being taken into consideration the evaluation and control unit generates the control signals $Si_{1...n}$ for the dosage unit.

Before the reperfusate is returned to the patient P via the blood flow path BL, with the aid of the analysis unit BA, an analysis of the "modified blood"/reperfusate is carried out to ensure that a correctly composed/modified reperfusate is being returned to the patient. For this, a second by-pass line A2 is provided immediately upstream of the blood return device BR which diverts some of the "modified blood"/reperfusate into the analysis unit BA. In the analysis unit BA, repeat sensor recording of the individual blood parameters $SEE_{1...n}$ takes place, which undergoes a nominal/actual comparison in the evaluation and control unit A/S. If deviations occur, the generated control signals $Si_1$, $Si_2$, $Si_3$, $Si_4$ are corrected in order influence the dosage unit $V_1$ to $V_4$.

Furthermore, on the basis of the blood analysis results BAE and the physiological patient parameters determined by the monitoring unit M, the evaluation and control unit generates control signals to control the conveying unit F determining the flow characteristics within the blood flow path BL, as well as the heat exchanger WT determining the temperature level of the reperfusate being infused into the patient, ultimately with the aim of tissue-protecting reperfusion of the "modified blood" back into the patient's blood circulation. In doing so, the parameters of the flow pressure, the flow rate, the pulsability, flow duration and temperature of the reperfusate are individually matched to the patient.

FIG. 4 shows a schematic blood diagram of a further embodiment of the invention. Sensor unit SEH, provides information obtained from the bodily fluid, more particularly blood, of a patient P. The sensor signals generated by the sensor unit SEH are forwarded to an analysis unit A which generates an analysis result representing the current state of the bodily fluid/blood. Based on at least one evaluation criterion, for example, the analysis result is evaluated by an evaluation and control unit A/S. The evaluation and control unit then generates control or regulating signals for the controlled activation of an operative unit KE which influences the bodily fluid and, in particular, can be composed of at least one of the following sub-units: units which add at least one substance to the bodily fluid MS, units which mechanically influence bodily fluid MM and units which thermally influence bodily fluid. Each of these units can be combined with joining units. Depending on the units that can be activated by the evaluation and control unit A/S, the bodily fluid of the patient P undergoes therapeutic manipulation or modification for the purpose of preventing ischaemic tissue damage.

The device in accordance with the invention is particularly compact and, if possible, in a single housing to assure as simple and fully automatic operation as possible. The processes of taking the blood, blood analysis, addition of at least one substance to the patient's blood to obtain "modified blood," and the reperfusion of the "modified blood" take place automatically and in situ, without further knowledge about the person to be resuscitated having to be available. The device obtains all information for successful reperfusion from the described sensor data sensors in the form of data from the automatic blood screening and sensor-detectable physiological data.

With the benefit of the device in accordance with the invention, controlled whole-body reperfusion can be carried out with which the duration of ischaemia, until irreversible damage to individual organs or even the entire body, can be considerably increased compared with the current narrow time limits.

LIST OF REFERENCES

BE Blood withdrawal device
BR Blood return device
BL Blood flow path
BA Analysis unit
R Reservoir unit
D Dosage unit
A1 Diversion line
A2 By-pass line
CIRD Basis module of the controlled integrated resuscitation device
F Conveying unit
O Oxygenator
G Gas blender
LF Leukocyte filter
A/S Evaluation/control unit
WT Heat exchanger
M Monitoring unit
$S_1$, $S_2$ ... Substance
$Si_1$ ... Control signal
$V_1$, $V_2$ ... Dosage unit, valve
MB Mixing container
$SE_1$, $SE_2$ ... Sensors
$SEE_1$, $SEE_2$ ... Sensor result
BAE Blood analysis result
A Analysis unit
SEH Sensor unit
KE Operative unit MS Unit for adding at least one substance to the bodily fluid
MM Unit for mechanically influencing the bodily fluid
MT Unit for thermally influencing the bodily fluid
A/S Control Unit

The invention claimed is:

1. A system providing treatment of cardiac arrest by withdrawing blood from a patient's or an animal's circulatory system during the cardiac arrest and introducing at least modified blood containing the withdrawn blood to which at least one substance has been added to provide whole body reperfusion of the circulatory system with the modified blood during the treatment of cardiac arrest comprising:
blood analysis means, for connection during the treatment to the blood withdrawn from the circulatory system, for determining during the treatment of the cardiac arrest, a plurality of parameters of the blood including at least $pO_2$, $pCO_2$, and pH representing a current condition of the patient or animal in cardiac arrest and an output representing the determination during the treatment,
storage means for storing during treatment of at least two substances from which the at least one substance is selected for treating the cardiac arrest,
means for selecting during the treatment, based on the analysis, a type and quantity of the at least one substance from the storage means which is added to the withdrawn blood to form the modified blood, which upon introduction into the circulatory system during the treatment of cardiac arrest lessens or prevents ischemic tissue damage; and
means for introducing during the treatment at least the modified blood into the circulatory system which provides the whole body reperfusion of the circulatory system to treat the cardiac arrest and which lessens or prevents the ischemic tissue damage during the treatment.

2. A system in accordance with claim 1, wherein the means for selecting, based on the determination of at least the $pO_2$, the $pCO_2$ and the pH, selects during the treatment a type and quantity of the at least one substance from the stored substances which is added to the blood to form the modified blood which upon introduction into the circulatory system during the cardiac arrest lessens or prevents ischemic tissue damage; and
the means for introducing introduces at least the modified blood into the circulatory system during the treatment which provides the whole body reperfusion of the circulatory system to treat the cardiac arrest, and which lessens or prevents ischemic tissue damage during the treatment of cardiac arrest.

3. A system in accordance with claim 2, comprising:
means for monitoring at least one physiological parameter of the patient or animal during the cardiac arrest and providing a representation of the at least one physiological parameter to the means for selecting which selects, based on the representation, a type and quantity of the at least one substance to form the modified blood.

4. A system in accordance with claim 3, comprising:
means for monitoring at least one physiological parameter of the patient or animal during the cardiac arrest and providing a representation of the at least one physiological parameter; and the means for selecting selects the at least one substance to form the modified blood which includes selecting a type and a quantity of the at least one substance based on the representation.

5. A system in accordance with claim 2, comprising:
means for monitoring at least one physiological parameter of the patient or animal during the cardiac arrest and providing a representation of the at least one physiological parameter; and the means for selecting selects the at least one substance to form the modified blood which includes selecting a type and a quantity of the at least one substance based on the representation.

6. A system in accordance with claim 2, wherein the means for storing stores a plurality of substances in solid, liquid or gaseous form, from which the at least one substance is selected by a type and quantity to be mixed with the blood to form the modified blood.

7. A system in accordance with claim 6, wherein the means for storing stores a plurality of substances in solid, liquid or gaseous form, from which the at least one substance is selected by a type and quantity to be mixed with the blood to form the modified blood.

8. A system in accordance with claim 2, wherein the means for selecting selects the at least one substance from at least one of an alkaline buffer solution, an acidic buffer solution, substances affecting sodium, potassium and/or calcium content, blood-thinning substances, free radical trapping agents, glutamate, aspartame, heart-rhythm-stabilizing substances, substances influencing leukocyte count and osmotically-active substances including salts, glucoses and proteins.

9. A system in accordance with claim 1, comprising:
a pump for pumping a regulated flow of the modified blood into the circulatory system.

10. A system in accordance with claim 9, comprising:
means for monitoring at least one physiological parameter of the patient or animal during the cardiac arrest and providing a representation of the at least one physiological parameter to the means for selecting which selects, based on the representation, a type and quantity of the at least one substance to form the modified blood.

11. A system in accordance with claim 10, comprising:
means for monitoring at least one physiological parameter of the patient or animal during the cardiac arrest and providing a representation of the at least one physiological parameter; and the means for selecting selects the at least one substance to form the modified blood which includes selecting a type and a quantity of the at least one substance based on the representation.

12. A system in accordance with claim 9, comprising:
means for monitoring at least one physiological parameter of the patient or animal during the cardiac arrest and providing a representation of the at least one physiological parameter; and the means for selecting selects the at least one substance to form the modified blood which includes selecting a type and a quantity of the at least one substance based on the representation.

13. A system in accordance with claim 9, wherein the means for storing stores a plurality of substances in solid, liquid or gaseous form, from which the at least one substance is selected by a type and quantity to be mixed with the blood to form the modified blood.

14. A system in accordance with claim 9, wherein the means for selecting selects the at least one substance from at least one of an alkaline buffer solution, an acidic buffer solution, substances affecting sodium, potassium and/or calcium content, blood-thinning substances, free radical trapping agents, glutamate, aspartame, heart-rhythm-stabilizing substances, substances influencing leukocyte count and osmotically-active substances including salts, glucoses and proteins.

15. A system in accordance with claim 1, comprising:
means for monitoring at least one physiological parameter of the patient or animal during the cardiac arrest and providing a representation of the at least one physiological parameter to the means for selecting which selects, based on the representation, a type and quantity of the at least one substance to form the modified blood.

16. A system in accordance with claim 15, comprising:
means for monitoring at least one physiological parameter of the patient or animal during the cardiac arrest and providing a representation of the at least one physiological parameter; and the means for selecting selects the at least one substance to form the modified blood which includes selecting a type and a quantity of the at least one substance based on the representation.

17. A system in accordance with claim 15, wherein the means for storing stores a plurality of substances in solid, liquid or gaseous form, from which the at least one substance is selected by a type and quantity to be mixed with the blood to form the modified blood.

18. A system in accordance with claim 15, wherein the means for selecting selects the at least one substance from at least one of an alkaline buffer solution, an acidic buffer solution, substances affecting sodium, potassium and/or calcium content, blood-thinning substances, free radical trapping agents, glutamate, aspartame, heart-rhythm-stabilizing substances, substances influencing leukocyte count and osmotically-active substances including salts, glucoses and proteins.

19. A system in accordance with claim 1 comprising:
withdrawing blood from the patient's or animal's circulatory system during the treatment of the cardiac arrest and introducing at least modified blood containing the blood to which at least one substance has been added during the treatment of the cardiac arrest to provide whole body reperfusion of the circulatory system with the modified blood.

20. A system in accordance with claim 19, comprising a pump for pumping the modified blood into the circulatory system.

21. A system in accordance with claim 20, comprising:
means for monitoring at least one physiological parameter of the patient or animal during the cardiac arrest and providing a representation of the at least one physiological parameter; and the means for selecting selects the at least one substance to form the modified blood which includes selecting a type and a quantity of the at least one substance based on the representation.

22. A system in accordance with claim 21, wherein the means for selecting selects the at least one substance from at least one of an alkaline buffer solution, an acidic buffer solution, substances affecting sodium, potassium and/or calcium content, blood-thinning substances, free radical trapping agents, glutamate, aspartame, heart-rhythm-stabilizing substances, substances influencing leukocyte count and osmotically-active substances including salts, glucoses and proteins.

23. A system in accordance with claim 21, wherein the means for monitoring monitors the at least one physiological parameter, at least one of mean arterial pressure, central nervous pressure, pulmonary artery pressure, oxygen saturation and blood temperature.

24. A system in accordance with claim 20, wherein the means for selecting selects the at least one substance from at least one of an alkaline buffer solution, an acidic buffer solution, substances affecting sodium, potassium and/or calcium content, blood-thinning substances, free radical trapping agents, glutamate, aspartame, heart-rhythm-stabilizing substances, substances influencing leukocyte count and osmotically-active substances including salts, glucoses and proteins.

25. A system in accordance with claim 19, comprising:
means for monitoring at least one physiological parameter of the patient or animal during the cardiac arrest and providing a representation of the at least one physiological parameter; and the means for selecting selects the at least one substance to form the modified blood which includes selecting a type and a quantity of the at least one substance based on the representation.

26. A system in accordance with claim 19, wherein the means for storing stores a plurality of substances in solid, liquid or gaseous form, from which the at least one substance is selected by a type and quantity to be mixed with the blood to form the modified blood.

27. A system in accordance with claim 19, comprising:
a heat exchanger in a blood flow path, disposed between a point of withdrawal of the blood from the circulatory system and point of return of at least the modified blood into the circulatory system which, based on the analysis, controls a temperature of at least the modified blood introduced into the circulatory system.

28. A system in accordance with claim 27, comprising means for controlling, based on the analysis, at least one of pressure, flow rate and temperature of at least the modified blood introduced into the circulatory system.

29. A system in accordance with claim 19, comprising means for providing an oxygen enrichment and a depletion means in a blood flow path, disposed between a point of withdrawal of the blood from the circulatory system and a point of return of at least the modified blood into the circulatory system for analyzing an amount of oxygen in the withdrawn blood and controlling with the oxygen and the depletion means, based on an analysis of oxygen in the withdrawn blood, oxygen present in at least the modified blood.

30. A system in accordance with claim 1, comprising:
means for mixing at least one stored substance with the withdrawn blood to form the modified blood.

31. A system in accordance with claim 1, wherein the means for storing stores a plurality of substances in solid, liquid or gaseous form, from which the at least one substance is selected by a type and quantity to be mixed with the blood to form the modified blood.

32. A system in accordance with claim 31, wherein the means for selecting selects the at least one substance from at least one of an alkaline buffer solution, an acidic buffer solution, substances affecting sodium, potassium and/or calcium content, blood-thinning substances, free radical trapping agents, glutamate, aspartame, heart-rhythm-stabilizing substances, substances influencing leukocyte count and osmotically-active substances including salts, glucoses and proteins.

33. A system in accordance with claim 1, wherein the means for selecting selects the at least one substance from at least one of an alkaline buffer solution, an acidic buffer solution, substances affecting sodium, potassium and/or calcium content, blood-thinning substances, free radical trapping agents, glutamate, aspartame, heart-rhythm-stabilizing substances, substances influencing leukocyte count and osmotically-active substances including salts, glucoses and proteins.

34. A system in accordance with claim 1, wherein:
the plurality of parameters of the blood further includes potassium content, calcium content, base excess, lactate value or glucose content.

\* \* \* \* \*